United States Patent [19]
Gleason et al.

[11] 4,000,154
[45] Dec. 28, 1976

[54] 3-SUBSTITUTED-6β-(AMINO- AND ACYLAMINO)-7-OXO-1,3-DIAZABICYCLO[3.2.0]-HEPTANE-2-CARBOXYLIC ACIDS AND DERIVATIVES THEREOF

[75] Inventors: John G. Gleason, Delran; Kenneth G. Holden, Haddonfield, both of N.J.; William F. Huffman, Malvern, Pa.

[73] Assignee: Smithkline Corporation, Philadelphia, Pa.

[22] Filed: Sept. 3, 1975

[21] Appl. No.: 610,517

[52] U.S. Cl. .................. 260/309.7; 260/239 A
[51] Int. Cl.$^2$ .................. C07D 487/04
[58] Field of Search .................. 260/309.7

[56] References Cited

OTHER PUBLICATIONS

Nagasawa et al. J. Org. Chem. 1972, vol. 37, pp. 516–519.
Bose et al. J. Org. Chem. 1973, vol. 38, pp. 3437–3438.
Bose et al. J. Chem. Soc. (London) C, 1971, pp. 188–190.
Deshpande et al. J. Chem. Soc. (London) C, 1966, pp. 1241–1242.
Earle et al. J. Chem. Soc. (London) C, 1969, pp. 2093–2098.
Golding et al. J. Chem. Soc. (London) Chem. Comm. 1973, pp. 293–294.
Lowe et al. J. Chem. Soc. (London) Chem. Comm. 1973, pp. 328–329.
Moll et al. Z. Naturforsch B, 1969, vol. 24, pp. 942–943.
Wolfe et el. Can. J. Chem. 1972, vol. 50, pp. 2902–2905.
Derwent Abstract No. 76051T of German Offen. 2,219,601.
Derwent Abstract No. 34499W of German Offen. 2,356,862.
Derwent Abstract No. 68222V of German Offen. 2,411,856.
Derwent Abstract No. 28433W of Netherlands Patent 7,313,896.

*Primary Examiner*—Natalie Trousof
*Attorney, Agent, or Firm*—Janice E. Williams; William H. Edgerton; Alan D. Lourie

[57] ABSTRACT

Novel bicyclic β-lactam penicillin analogs which have antibacterial activity and intermediates for the synthesis thereof are disclosed. In particular, 3-acetyl-7-oxo-6β-phenoxyacetylamino-1,3-diazabicyclo[3.2.0]heptane-2-carboxylic acid and derivatives thereof are prepared.

16 Claims, No Drawings

3-SUBSTITUTED-6β-(AMINO- AND ACYLAMINO)-7-OXO-1,3-DIAZABICYCLO[3.2.0]-HEPTANE-2-CARBOXYLIC ACIDS AND DERIVATIVES THEREOF

This invention relates to novel analogs of penicillins which have a 1,3-diazabicyclo[3.2.0]heptan-7-one nucleus. These compounds have antibacterial activity.

BACKGROUND OF THE INVENTION

The basic penicillin nucleus is a 4-thia-1-azabicyclo[3.2.0]heptan-7-one ring system having the skeletal structure:

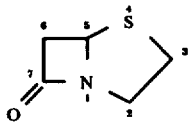

Compounds having this ring system have been the object of intense research and numerous scientific articles and patents over the past two decades.

Within the last few years, attention has been directed to the synthesis of compounds having analogous ring systems. Among these penicillin analogs are 1-azabicyclo[3.2.0]heptane-7-one systems [Moll et al., *Z. Naturforsch B* 24:942 (1969); Earle et al., *J. Chem. Soc. C* 2093 (1969) and Lowe et al., *J. Chem. Soc. Chem. Comm.* 328 (1973)]; 4-oxa-1-azabicyclo[3.2.0]heptan-7-one systems [Deshpande et al., *J. Chem. Soc. C* 1241 (1966); Wolfe et al., *Can. J. Chem* 50:2902 (1972); Golding et al., *J. Chem. Soc. Chem. Comm.* 293 (1973); German Offenlegung-schriften 2,219,601, 2,356,862 and 2,411,856; Japanese Patent 9,007,263 and Netherlands Patent 7,313,896]; 1,4-diazabicyclo[3.2.0]heptan-7-one systems [Bose et al., *J. Org. Chem.* 38:3437 (1973) and German Offenlegungschrift 2,219,601] and a 3-thia-1-azabicyclo[3.2.0]heptan-7-one system [Bose et al., *J. Chem. Soc. C* 188 (1971)].

Compounds containing the 1,3-diazabicyclo[3.2.0]heptan-7-one nucleus have now been prepared by a totally synthetic method.

DESCRIPTION OF THE INVENTION

The compounds of this invention are 1,3-diazabicyclo[3.2.0]heptan-7-one penicillin analogs which are represented by the following structural formula:

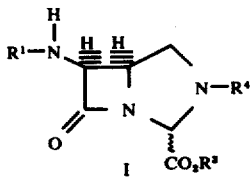

in which:
$R^1$ is hydrogen or

$R^2$ is phenyl; phenoxymethyl; benzyl; α-aminobenzyl; α-hydroxybenzyl; α-carboxybenzyl; phenyl substituted with lower alkyl of from one to four carbon atoms, lower alkoxy of from one to four carbon atoms, trifluoromethyl, halo or hydroxy; or benzyl substituted on the phenyl ring with lower alkyl of from one to four carbon atoms, lower alkoxy of from one to four carbon atoms, trifluoromethyl, halo or hydroxy;

$R^3$ is hydrogen or an easily removable ester protecting group; and $R^4$ is alkanoyl of from one to five carbon atoms; alkoxycarbonyl of from two to five carbon atoms; haloacetyl; dihaloacetyl; benzoyl; benzoyl substituted with lower alkyl of from one to four carbon atoms, lower alkoxy of from one to four carbon atoms, trifluoromethyl or halo; phenylacetyl; phenylacetyl substituted on the phenyl ring with lower alkyl of from one to four carbon atoms, lower alkoxy of from one to four carbon atoms, trifluoromethyl or halo; methanesulfonyl; ethanesulfonyl; benzenesulfonyl; α-toluenesulfonyl or p-toluenesulfonyl.

It will be recognized that the 2-carboxylic acid group of the compounds of formula I, when $R^3$ is hydrogen, may be readily converted to a non-toxic pharmaceutically acceptable salt, for example those formed with the alkali metals such as sodium or potassium, the alkaline earth metals such as calcium or with the ammonium cation. These salts are prepared by standard methods and are also considered as objects of this invention.

The term "easily removable ester protecting group" is one which has acquired a definite meaning within the penicillin, cephalosporin and peptide art. Many such groups are known which are used to protect the carboxyl group during subsequent chemical reactions and are later removed by standard methods to give the free carboxylic acid. Known ester protecting groups include 2,2,2-trichloroethyl, $C_4$-$C_6$-tertiary alkyl, $C_5$-$C_7$-tertiary alkenyl, $C_5$-$C_7$-tertiary alkynyl, $C_1$-$C_6$-alkanoylmethyl, N-phthalimidomethyl, benzoylmethyl, naphthoylmethyl, furoylmethyl, thienoylmethyl, nitrobenzoylmethyl, halobenzoylmethyl, methylbenzoylmethyl, methanesulfonylbenzoylmethyl, phenylbenzoylmethyl, benzyl, nitrobenzyl, methoxybenzyl, benzyloxymethyl, nitrophenyl, methoxyphenyl, benzhydryl, trityl, trimethylsilyl, triethylsilyl and the like. The choice of an ester protecting group is well within the ability of one skilled in the art. Factors which are considered include the subsequent reaction conditions the group must withstand and the conditions desired for removing the protecting group. Because the novelty of this invention lies within the new bicyclic nucleus, the choice of a protecting group is not critical to the invention.

Compounds within the scope of formula I which are also part of this invention are those in which:

A. $R^3$ is 2,2,2-trichloroethyl, t-butyl, benzyl, benzhydryl, benzyloxymethyl, p-nitrophenyl, p-methoxyphenyl, p-nitrobenzyl and p-methoxybenzyl.

B. $R^3$ is as in A and $R^4$ is acetyl, propionyl, ethoxycarbonyl, p-anisoyl, p-toluoyl or methanesulfonyl.

C. $R^3$ and $R^4$ are as in B and $R^1$ is hydrogen.

D. $R^3$ and $R^4$ are as in B and $R^1$ is

or in particular phenoxymethylcarbonyl.

E. R³ is hydrogen and R⁴ is acetyl, propionyl, ethoxycarbonyl, p-anisoyl, p-toluoyl or methanesulfonyl.

F. R³ and R⁴ are as in E and R¹ is hydrogen.

G. R³ and R⁴ are as in E and R¹ is

or in particular phenoxymethylcarbonyl.

The compounds of formula I are prepared as shown in Scheme 1 below in which R² and R⁴ are defined as above, R⁵ is an easily removable amine protecting group, x is halogen, preferably chloro, and R³ is an easily removable ester protecting group.

The term "an easily removable amine protecting group" is a well known term which includes many groups known and used in the penicillin, cephalosporin or peptide synthesis art. These groups include trityl, t-butoxycarbonyl, trichloroethoxycarbonyl, benzyloxycarbonyl, methyl acetoacetate adduct and the like. Divalent amine protecting groups include phthaloyl, imines and the like. The choice of the protecting group depends on various factors including the subsequent chemical reaction conditions and the conditions desired for removing the protecting group. The choice of the protecting group to be used is within the ordinary ability of one skilled in the art.

such as sodium azide gives the corresponding azidomethyl compound VI. The amine protective group is removed, for example by treatment of VI with trifuoroazetic acid, and the resulting amino compound is acylated according to standard procedures to give VII. Reduction of VII with subsequent reaction of the aminomethyl compound thus formed with a glyoxalic acid derivative, the carboxylic acid function being suitably protected with an easily removable ester protecting group, gives compound VIII. Treatment of VIII with an acyl halide (R⁴-X) gives the 1,3-diazabicyclo compounds of formula I where R¹ is R²CO- and R³ is an easily removable easter protecting group. When R⁴ is formyl, the corresponding compounds of formula I where R¹ is R²CO- and R³ is an easily removable ester protecting group are also prepared by treatment of VIII with formyl imidazole in the presence of a catalytic amount of imidazole hydrochloride. Cleavage of the ester protecting group gives the compounds of formula I where R¹ is R²CO- and R³ is hydrogen.

when the amine protective group selected is itself a group desired as a 6-substituent in the final product, viz. one of the formula R²CO- where R² is defined as above, the steps of deblocking of the amine function and subsequent acylation can be eliminated from the reaction sequence depicted in Scheme 1.

When R¹ is hydrogen, the corresponding compounds of formula I are, preferably, prepared by removal of the

SCHEME 1

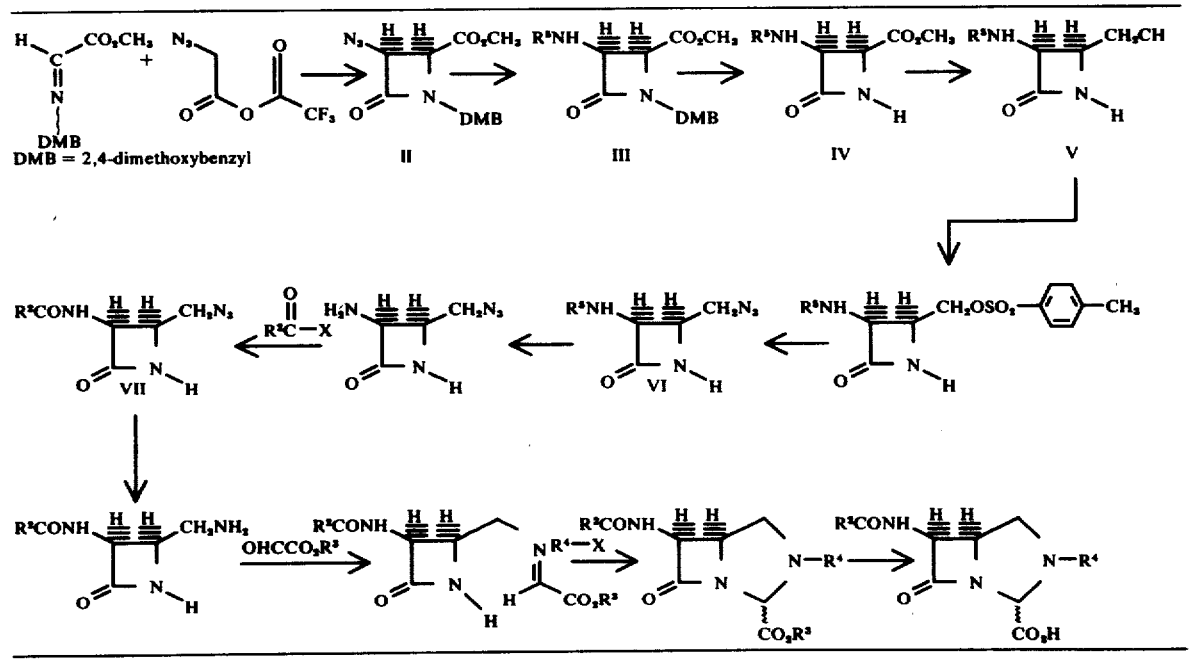

According to Scheme 1, when the imine, which results from the condensation of methyl glyoxalate and 2,4-dimethoxybenzylamine, is allowed to react with a mixed anhydride of azidoacetic acid, azetidinone II is obtained. Hydrogenation of this compound gives the corresponding amino derivative which can be protected with an amine protecting group by standard methods to give compound III. Treatment of III with potassium persulfate results in the removal of the dimethoxybenzyl group to give compound IV which upon reduction, for example with sodium borohydride, gives V. Reaction of the tosylate derivative of v with an azide amine and carboxylic acid protective groups from a 3-substituted-6β-benzyloxycarbonylamino-7-oxo-1,3-diazabicyclo[3.2.0]-heptane-2-carboxylic acid benzyl ester, for example by hydrogenolysis. The 3-substituted-6β-benzyloxycarbonylamino-7-oxo-1,3-diazabicyclo[3.2.0]heptane-2-carboxylic acid benzyl esters are prepared by the methods described above.

Alternatively, the 3-azido azetidinone II may be converted to a 3-amino-2-tosylmethyl derivative by cleavage of the 2,4-dimethoxybenzyl group followed by reduction of the ester function, conversion of the product hydroxymethyl compound to the tosylate and reduction of the azide moiety, all as described above. The resulting 3-amino azetidinone may then be acylated or protected as required and converted to the desired 1,3-diazabicyclo[3.2.0]heptane compound.

The starting materials for the compounds of this invention are commercially available, prepared by known methods or prepared as described herein.

It is recognized that, due to asymmetric carbon atoms both in the bicyclic β-lactam ring system and in some acyl sidechains, stereoisomers will exist. All of these isomers, including separated isomers and mixtures thereof, are included within the scope of this invention.

The compounds of this invention are useful as antibacterial agents. For example, the compound 3-acetyl-7-oxo-6β-phenoxyacetylamino-1,3-diazabicyclo[3.2.0-]heptane-2-carboxylic acid exhibited activity against *Staphylococcus aureus, B. subtilis* and other bacteria in in vitro testing. In addition, the compounds of formula I where $R^1$ is hydrogen are useful as chemical intermediates in the preparation of novel bicyclic β-lactams which have antibacterial activity.

Pharmaceutical compositions having antibacterial activity which comprise a pharmaceutical carrier containing an active but non-toxic quantity of a compound of formula I as well as methods of combatting bacterial infections by administering such a composition to an infected host in a non-toxic amount sufficient to combat such infections are also objects of this invention. The preferred route of administration is by parenteral injection, such as subcutaneously, intramuscularly or intravenously, of suitably prepared sterile solutions or suspensions containing an effective, non-toxic amount of the new cephalosporin compound.

The compounds of formula I are formulated and administered in the same manner as other cephalosporins. The dosage regimen comprises administration, preferably by injection, of an active but non-toxic quantity of a compound of formula I. The precise dosages are dependent upon the age and weight of the subject and on the infection being treated and can be determined by those skilled in the art based on the data disclosed herein compared with that available to the art attained with known cephalosporins.

The following examples illustrate the invention, but are not to be construed as limiting the scope thereof. All temperatures are in degrees Centigrade (° C.) unless otherwise indicated.

PREPARATION 1

Methyl cis-3-azido-1-(2,4-dimethoxybenzyl)-4-oxoazetidine-2-carboxylate

To a mixture containing 16.82 g (0.101 mole) of 2,4-dimethoxybenzylamine and anhydrous magnesium sulfate in 150 ml of methylene chloride at 25° was added a solution of 10.05 g (0.114 mole) of methyl glyoxalate in 20 ml of methylene chloride. The reaction mixture was stirred at room temperature overnight (15 hours) and then was filtered and the solvents were removed in vacuo to afford the imine as a dark orange gum.

To a solution of 15.1 g (0.149 mole) of azidoacetic acid in 130 ml of anhydrous methylene chloride at 0° (ice bath) was added dropwise 21.0 ml (0.15 mole) of trifluoroacetic anhydride. This mixture was stirred at 0° for 15 min and then 20.8 ml (0.15 mole) of triethylamine was added dropwise. Stirring was continued for an additional 45 min and then the entire reaction mixture was transferred under argon into an addition funnel which was cooled externally by dry ice. The addition funnel was attached to a flask containing the imine from above, 200 ml of anhydrous methylene chloride and 20.8 ml (0.15 mole) of triethylamine. The solution of the mixed anhydride was added dropwise from the addition funnel to the solution of imine at 0°. Stirring was continued at 0° for 1 hour and then the dark reaction mixture was transferred to a separatory funnel and washed with water aqueous sodium bicarbonate and brine and dried over anhydrous magnesium sulfate. The solvents were removed in vacuo and the residue was chromatographed on 300 g of silica gel (70-230 mesh) affording an off-white solid which was further purified by trituration with ether to give the title compound as a white solid; tlc: benzene:ethyl acetate (1:1), silica gel GF, Rf = 0.64; mp 82°-84° (ethyl acetatehexane).

PREPARATION 2

Methyl cis-4-oxo-3-phenoxyacetaylaminoazetidiine-2-carboxylate

A mixture containing 10.0 g (0.0312 mole) of methyl cis-3-azido-1-(2,4-dimethoxybenzyl)-4-oxoazetidine-2-carboxylate, 1.0 g of 10% palladium on carbon and 200 ml of ethanol was hydrogenated at 60 psi of hydrogen at 40°-45° for 2 hours. The reaction mixture was allowed to cool to 25° and was filtered through celite. After removing the solvents in vacuo there remained a clear, yellow gum. The crude amine was taken up in 100 ml of anhydrous methylene dichloride and was cooled to 0° in an ice bath. To this solution was added 4.32 ml (0.0312 mole) of triethylamine followed by the slow addition of a solution of 5.32 g (0.0312 mole) of phenoxyacetyl chloride in 40 ml of methylene dichloride. The mixture was stirred at 0° for 1 hour then extracted successively with water, aqueous hydrochloric acid, aqueous sodium bicarbonate and brine and was dried over anhydrous magnesium sulfate. Filtration followed by removal of the solvent in vacuo afforded a yellow solid. This material was partially dissolved in ether, cooled to −25° and filtered to give methyl cis-1-(2,4-dimethoxybenzyl)-4-oxo-3-phenoxyacetylaminoazetidine-2-carboxylate as a white solid; tlc: benzene:ethyl acetate (1:1), silica gel, Rf = 0.38; mp 115.5°-116.0° (ethyl acetate-hexane).

To 900 ml of acetonitrile, which had been thoroughly degassed with argon, was added 30.0 g (0.070 mole) of methyl cis-1-(2,4-dimethoxybenzyl)-4-oxo-3-phenoxyacetyl-aminoazetidine-2-carboxylate and the solid was rinsed into the reaction vessel with an additional 50 ml of degassed acetonitrile. This solution was heated to 78° under argon and to it was added a degassed solution of 75.6 g (0.28 mole) of potassium persulfate and 37.5 g (0.14 mole) of sodium monohydrogen phosphate in 1400 ml of water. Addition of the aqueous solution was made in six portions of 250 ml over a period of 1 hour while maintaining the external temperature between 78° and 82°. After cooling the reaction mixture, the acetonitrile was removed by evaporation. Sodium chloride was added to the concentrated reaction mixture and it was extracted four times with ethyl acetate. The combined ethyl acetate extracts were dried ($MgSO_4$), filtered and concentrated in vacuo to approximately 100-200 ml. Addition of ether (ca. 300 ml) followed by low temperature (—25° C) crystallization afforded the title compound; tlc: silica gel GF, ethyl acetate, Rf = 0.44; ethyl acetate:benzene (1:1),RF = 0.21; mp 140°–141° (ethyl acetate-hexane).

PREPARATION 3 cis-2-Hydroxymethyl-4-oxo-3-phenoxyacetylaminoazetidine

To a solution of 13.5 g (0.049 mole) of methyl cis-4-oxo-3-phenoxyacetylaminoazetidine-2-carboxylate in 975 ml of tetrahydrofuran and 100 ml of water at 0° (ice bath) was added a cold solution of 3.75 g (0.099 mole) of sodium borohydride in 250 ml of water over a period of 10 min. The solution was stirred at 0° for 40 min and then glacial acetic acid was added dropwise until hydrogen evolution ceased. Solid sodium bicarbonate and sodium chloride were added and this mixture was extracted five times with 250 ml portions of ethyl acetate. After drying the combined extracts (MgSO$_4$), the solvent was removed in vacuo. The resulting residue was dissolved in ethyl acetate, clarified with Norite and allowed to crystallize to give the title compound; tlc; ethyl acetate, silica gel GF, Rf = 0.10; mp 153°–154° (ethyl acetate).

PREPARATION 4 cis-2-azidomethyl-4-oxo-3-phenoxyacetylaminoazetidine

To a solution of 4.30 g (0.022 mole) of 98% p-toluenesulfonyl chloride in 24 ml of anhydrous pyridine at 0° (ice bath) was added 2.64 g (0.011 mole) of cis-2-hydroxymethyl-4-oxo-3-phenoxyacetylaminoazetidine in one portion. The solution was stirred at 0° for 3 hours then was stored at —25° overnight. After warming to 0°, 1.0 ml of 85% lactic acid was added and stirring was continued for 1 hour. The reaction mixture was poured into ethyl acetate and extracted successively with water, dilute aqueous hydrochloric acid, aqueous sodium bicarbonate and brine and was dried (MgSO$_4$). Filtration followed by removal of the solvent in vacuo resulted in a yellow solid. Clarification of a hot solution of this material in ethyl acetate (375 ml), followed by the addition of hexane (200 ml) and recrystallization afforded cis-4-oxo-3-phenoxyacetylamino-2-p-toluenesulfonyloxymethyl-azetidine; tlc: ethyl acetate, silica gel GF, Rf = 0.47; mp 136°(dec.).

A mixture containing 1.131 g (2.8 mmole) of cis-4-oxo-3-phenoxyacetylamino-2-p-toluenesulfonyloxymethyl-azetidine, 0.961 g (14.8 mmole) of sodium azide and 25 ml of anhydrous N,N-dimethylformamide was heated under argon at 40° for 6 hours then at ambient temperature for 24 hours. The reaction mixture was poured into ethyl acetate and was washed with water. The combined aqueous washes were extracted once with ethyl acetate and the ethyl acetate fractions were combined and extracted with brine. After drying the ethyl acetate solution (MgSO$_4$) and filterng, the solvent was removed in vacuo to afford to a yellow semi-crystalline residue. This residue was slurried in methylene dichloride and chromatographed on 25 g of silica gel (70–230 mesh). The 1:1 ethyl acetate:methylene dichloride fractions afforded the title compound; tlc: ethyl acetate, silica gel GF, Rf = 0.38; mp 142°–143°(dec) (ethyl acetate-hexane).

PREPARATION 5 cis-2-Azidomethyl-3-t-butoxycarbonylamino-4-oxoazetidine

A mixture containing 10.0 g (0.0312 mole) of methyl cis-3-azido-1-(2,4-dimethoxybenzyl)-4-oxoazetidine-2-carboxylate, 1.0 g of 10% palladium on carbon and 200 ml of ethanol was hydrogenated for 2 hours at 40°–45° and 60 psi of hydrogen. The reaction mixture was allowed to cool to 25° and was filtered through filter-aid. After removing the solvents in vacuo there remained methyl cis-3-amino-1-(2,4-dimethoxybenzyl)-4-oxoazetidine-2-carboxylate.

A solution of 5.5 g (18.8 mmole) of methyl cis-3-amino-1-(2,4-dimethoxybenzyl)-4-oxoazetidine-2-carboxylate in 100 ml of dry toluene was cooled to —78° and 2.5ml (18.8 mmole) of triethylamine was added followed by rapid addition of 35 ml (42mmole) of a 12% solution of phosgene in benzene. The mixture was stirred 15 min at —78°, 3 hours at —45°(acetonitrile-dry ice), then warmed to room temperature and concentrated to half volume in vacuo. To the resulting solution was added 50 ml of t-butanol and the mixture was stirred at room temperature overnight. The solvents were removed in vacuo and the residue diluted with ethyl acetate and filtered. The filtrate was transferred to a separatory funnel and washed with 5% aqueous sodium bicarbonate, 5% hydrochloric acid and brine, dried (MgSO$_4$) and evaporated to dryness. Recrystallization of the crude, crystalline product from ether gave methyl cis-3-t-butoxycarbonylamino-1-(2,4-dimethoxybenzyl)-4-oxoazetidine-2-carboxylate, mp 134°–135°.

A solution of 10.5 g (26.7 mmole) of methyl 3-t-butoxycarbonylamino-1-(2,4-dimethoxybenzyl)-4-oxoazetidine-2-carboxylate in 500 ml of acetonitrile was degassed with argon and warmed to 80°. A degassed solution of 15 g (55.5 mmole) of potassium persulfate and 7.5 g (28 mmole) of sodium monohydrogen phosphate in 150 ml of water was added in five portions over 1 hour. The reaction was stirred at 80°–85° under argon for 2–3 hours until all starting material had disappeared (tlc). The reaction mixture was cooled, concentrated in vacuo and shaken with ethyl-acetate water. The organic phase was washed with dilute hydrochloric acid, aqueous sodium bicarbonate solution and brine, dried (MgSO$_4$) and evaporated to dryness. The residue was chromatographed on silica gel with 1:1 benzene:ethyl acetate to afford pure product which crystallized from ethyl acetate-hexane to give methyl cis-3-t-butoxycarbonylamino-4-oxoazetidine-2-carboxylate, mp 140°–144°.

Sodium borohydride reduction of methyl cis-3-t-butoxycarbonylamino-4-oxoazetidine-2-carboxylate as described in Preparation 3, followed by conversion of the 2-hydroxymethylazetidine product to the p-toluene-sulfonate derivative, mp 160°–162°(d), and reaction of the derivative with sodium azide as described in Preparation 4 gives the title compound.

PREPARATION 6 cis-3-Amino-2-azidomethyl-4-oxoazetidine cis-2-Azidomethyl-3-t-butoxycarbonylamino-4-oxoazetidine(ca. 1 g) is dissolved in 2 ml of methylene chloride and the solution is cooled to 0° and treated with 0.5 ml of trifluoroacetic acid for 30 minutes at 0°. The solution is washed with 5% aqueous sodium bicarbonate and extracted with dilute hydrochloric acid.

The aqueous phase is neutralized and extracted with ethyl acetate. Evaporation of the solvent gives the title compound.

PREPARATION 7 cis-3-Amino-4-oxo-2-p-toluenesulfonyloxymethylazetidine

A degassed solution of 3.8 g (0.012 mole) of methyl cis-3-azido-1-(2,4-dimethoxybenzyl)-4-oxoazetidine-2-carboxylate was treated with potassium persulfate and sodium monohydrogen phosphate as described in Preparation 2 to give methyl cis-3-azido-4-oxoazetidine-2-carboxylate which was purified by chromatography on silica gel with benzene-ethyl acetate as eluant.

Methyl cis-3-azido-4-oxoazetidine-2-carboxylate was reduced with sodium borohydride as described in Preparation 3 and the product was chromatographed on silica gel with ethyl acetate as eluant to give cis-3-azido-2-hydroxymethyl-4-oxoazetidine.

cis-3-Azido-4-oxo-2-p-toluenesulfonyloxymethylazetidine was prepared from cis-3-azido-2-hydroxymethyl-4-oxoazetidine according to the procedure of Preparation 4.

Zinc dust (2.0 g, 0.03 mole) was slowly added with cooling to a solution of 5.0 g (0.011 mole) of cis-3-azido-4-oxo-2-p-toluenesulfonyloxymethylazetidine in 50 ml of 50% aqueous acetic acid. The reaction mixture was stirred for 30 minutes and filtered. The solids were washed with water and the filtrate was saturated with hydrogen sulfide, filtered and concentrated to near dryness. The residue was dissolved in ethyl acetate-water and the pH as adjusted to 8.0 by addition of sodium carbonate and sodium hydroxide solutions. The layers were separated and the aqueous phase was extracted twice with ethyl acetate. The extracts were combined, dried (MgSO$_4$) and evaporated to dryness to give the title compound.

EXAMPLE 1

3-Acetyl-7-oxo-6β-phenoxyacetylamino-1,3-diazabicyclo-[3.2.0]heptane-2-carboxylic acid A suspension of 0.499 g (1.81 mmole) of cis-2-azidomethyl-4-oxo-3-phenoxyacetylaminoazetidine and 0.189 g of 10% palladium on carbon in 25 ml of absolute ethanol was hydrogenated at atmoshperic pressure and at 40° for 1 hour. The solution was filtered through celite and the solvent was removed in vacuo to afford a colorless gum which was dissolved in 15 ml of methylene dichloride. Anhydrous magnesium sulfate was added followed by addition of a solution of 0.314 g (1.91 mmole) of benzyl glyoxalate in 10 ml of methylene dichloride. The reaction mixture was stirred at room temperature under argon for 2.5 hours then was allowed to stand at 0° overnight. After filtering the reaction mixture, the solvents were removed in vacuo to give a semi-crystalline residue which was recrystallized from ethyl acetate-hexane to given N-(cis-4-oxo-3-phenoxyacetylamino-2-azetidinylmethyl)iminoacetic acid benzyl ester as a colorless solid.

To a solution of 50 mg (0.13 mmole) of N-(cis-4-oxo-3-phenoxyacetylamino-2-azetidinylmethyl)iminoacetic acid benzyl ester in 1.8 ml of anhydrous methylene dichloride at 0° under argon was added 16 μl (0.20 mmole) of anhydrous pyridine followed by 14 μl (0.20 mmole) of acetyl chloride. After the reaction mixture had been stirred at 0° for 1 hour, ethyl acetate was added and the resulting mixture as rapidly suction filtered through a sintered glass funnel containing 1.0 g of silica gel. The solvents were removed in vacuo to afford a semi-crystalline yellow gum which was recrystallized from ether-methanol to give 3-acetyl-7-oxo-6β-phenoxyacetylamino-1,3-diazabicyclo[3.2.0]heptane-2-carboxylic acid benzyl ester as a mixture of C-2 epimers; tlc: ethyl acetate, silica gel GF, Rf = 0.55; mp 148°–150°.

A suspension of 14 mg of 10% palladium on carbon and 28 mg (0.064 mmole) of 3-acetyl-7-oxo-6β-phenoxy-acetylamino-1,3-diazabicyclo[3.2.0]heptane-2-carboxylic acid benzyl ester in ca. 2 ml of anhydrous ethyl acetate was hydrogenated at room temperature and atmospheric pressure for 1 hour. The reaction mixture was filtered through celite and the solvents were removed in vacuo to afford the title compound; tlc: 90:8:2 methylene chloride:methanol:acetic acid, silica gel GF, Rf = 0.31.

EXAMPLE 2

3-Acetyl-6β-amino-7-oxo-1,3-diazabicyclo[3.2.0]heptane-2-carboxylic acid

Reaction of cis-3-amino-4-oxo-2-p-toluenesulfonyloxymethylazetidine with benzyl chloroformate according to the procedure described in Preparation 2 for reaction of methyl cis-3-azido-1-(2,4-dimethoxybenzyl)-4-oxoazetidine-2-carboxylate and phenoxyacetyl chloride gives cis-3-benzyl-oxycarbonylamino-4-oxo-2-p-toluenesulfonyloxymethylazetidine.

cis-3-Benzyloxycarbonylamino-4-oxo-2-p-toluenesulfonyloxymethylazetidine is converted to cis-2-azidomethyl-3-benzyloxycarbonylamino-4-oxoazetidine as described in Preparation 4.

cis-2-Azidomethyl-3-benzyloxycarbonylamino-4-oxoazetidine is treated with zinc dust in 50% aqueous acetic acid as described in Preparation 7. Reaction of the crude reduction product with benzyl glyoxalate in methylene dichloride as described in the procedure of Example 1 gives N-(cis-3-benzyloxycarbonylamino-4-oxo-2-azetidinyl-methyl)iminoacetic acid benzyl ester which, when treated with acetyl chloride according to the procedure of Example 1, gives 3-acetyl-6β-benzyloxycarbonylamino-7-oxo-1,3-diazabicyclo[3.2.0]heptane-2-carboxylic acid benzyl ester.

Hydrogenolysis of 3-acetyl-6β-benzyloxycarbonyl-amino-7oxo-1,3-diazabicyclo[3.2.0]heptane-2-carboxylic acid benzyl ester as described in Example 1 gives the title compound.

EXAMPLE 3

3-Acetyl-6β-mandeloylamino-7-oxo-1,3-diazabicyclo[3.2.0]-heptane-2-carboxylic acid When cis-3-amino-4oxo-2-p-toluenesulfonyloxymethylazetidine is reacted with O-benzylmandeloyl chloride according to the procedure described in Preparation 2 and the product thus formed is subsequently converted to the corresponding 2-azidomethyl compound, the 2-azidomethyl compound is reduced with zinc and acetic acid then reacted with benzyl glyoxalate and the product is treated with acetyl chloride, 3-acetyl-6β-(α-benzyloxyphenyl-acetylamino)-7-oxo-1,3-diazabicyclo[3.2.0]heptane-2-carboxylic acid benzyl ester is obtained. Hydrogenolysis of the benzyl protective groups as previously described gives the title compound.

EXAMPLE 4

Reaction of cis-3-amino-4-oxo-2-p-toluenesulfonyloxy-methylazetidine with a halide of an acid listed below, suitably protected as necessary:

benzoic acid
p-toluic acid
4-ethylbenzoic acid
4-t-butylbenzoic acid
m-anisic acid
4-n-butoxybenzoic acid
2-chlorobenzoic acid
4-bromobenzoic acid
4-hydroxybenzoic acid
3-trifluoromethylbenzoic acid
phenylacetic acid
α-aminophenylacetic acid α-carboxyphenylacetic acid
4-fluorophenylacetic acid
3-hydroxyphenylacetic acid
4-trifluoromethylphenylacetic acid followed by conversion of the products thus formed to the 1,3-diazabicyclo[3.2.0]heptane-2-carboxylic acid benzyl esters by the sequence of synthetic steps described hereinabove and particularly in Example 3 with removal of the appropriate protective groups when necessary by standard procedures gives the following compounds of this invention:

3-acetyl-6β-benzoylamino-7oxo-1,3-diazabicyclo[3.2.0]heptane-2-carboxylic acid benzyl ester
3-acetyl-7-oxo-6β-(p-toluoylamino)-1,3-diazabicyclo[3.2.0]heptane-2-carboxylic acid benzyl ester
3-acetyl-6β-(4-ethylbenzoylamino)-7-oxo-1,3-diazabicyclo[3.2.0]heptane-2-carboxylic acid benzyl ester
3-acetyl-6β-(4-t-butylbenzoylamino)-7-oxo-1,3-diazabicyclo[3.2.0]heptane-2-carboxylic acid benzyl ester
3-acetyl-6β-(m-anisoylamino)7-oxo-1,3-diazabicyclo[3.2.0]heptane-2-carboxylic acid benzyl ester
3-acetyl-6β-(4-n-butoxybenzoylamino)-7-oxo-1,3-diazabicyclo[3.2.0]heptane-2-carboxylic acid benzyl ester
3-acetyl-6β-(2-chlorobenzoylamino)-7-oxo-1,3-diazabicyclo[3.2.0]heptane-2-carboxylic acid benzyl ester
3-acetyl-6β-(4-bromobenzoylamino)-7-oxo-1,3-diazabicyclo[3.2.0]heptane-2-carboxylic acid benzyl ester
3-acetyl-6β-(4-hydroxybenzoylamino)-7-oxo-1,3-diazabicyclo[3.2.0]heptane-2-carboxylic acid benzyl ester
3-acetyl-7-oxo-6β-(3-trifluoromethylbenzoylamino)-7-oxo-1,3-diazabicyclo[3.2.0]-heptane-2-carboxylic acid benzyl ester
3-acetyl-7-oxo-6β-phenylacetylamino-7-oxo-1,3-diazabicyclo[3.2.0]heptane-2-carboxylic acid benzyl ester
3-acetyl-6β-(α-aminophenylacetylamino)-7-oxo-1,3-diazabicyclo[3.2.0]heptane-2-carboxylic acid benzyl ester
3-acetyl-6β-(α-carboxyphenylacetylamino)-7-oxo-1,3-diazabicyclo[3.2.0]heptane-2-carboxylic acid benzyl ester
3-acetyl-6β-(4-fluorophenylacetylamino)-7-oxo-1,3-diazabicyclo[3.2.0]heptane-2-carboxylic acid benzyl ester
3-acetyl-6β-(3-hydroxyphenylacetylamino)-7-oxo-1,3-diazabicyclo[3.2.0]heptane-2-carboxylic acid benzyl ester
3-acetyl-7-oxo-6β-(4-trifluoromethylphenylacetylamino)-7-oxo-1,3-diazabicyclo[3.2.0]heptane-2-carboxylic acid benzyl ester.

Removal of the benzyl ester protecting group as previously described or by other standard methods gives the carboxylic acid compounds of this invention listed below:

3-acetyl-6β-benzoylamino-7-oxo-1,3-diazabicyclo[3.2.0]heptane-2-carboxylic acid
3-acetyl-7-oxo-6β-(p-toluoylamino)-1,3-diazabicyclo[3.2.0]heptane-2-carboxylic acid
3-acetyl-6β-(4-ethylbenzoylamino)-7-oxo-1,3-diazabicyclo[3.2.0]heptane-2-carboxylic acid
3-acetyl-6β-(4-t-butylbenzoylamino)-7-oxo-1,3-diazabicyclo[3.2.0]heptane-2-carboxylic acid
3-acetyl-6β-(m-anisoylamino)-7-oxo-1,3-diazabicyclo[3.2.0]heptane-2-carboxylic acid
3-acetyl-6β-(4-n-butoxybenzoylamino)-7-oxo-1,3-diazabicyclo[3.2.0]heptane-2-carboxylic acid
3-acetyl-6β-(2-chlorobenzoylamino)-7-oxo-1,3-diazabicyclo[3.2.0]heptane-2-carboxylic acid
3-acetyl-6β-(4-bromobenzoylamino)-7-oxo-1,3-diazabicyclo[3.2.0]heptane-2-carboxylic acid
3-acetyl-6β-(4-hydroxybenzoylamino)-7-oxo-1,3-diazabicyclo[3.2.0]heptane-2-carboxylic acid
3-acetyl-7-oxo-6β-(3-trifluoromethyl-benzoylamino)-7-oxo-1,3-diazabicyclo[3.2.0]-heptane-2-carboxylic acid
3-acetyl-7-oxo-6β-phenylacetylamino-7-oxo-1,3-diazabicyclo[3.2.0]heptane-2-carboxylic acid
3-acetyl-6β-(α-aminophenylacetylamino)-7-oxo-1,3-diazabicyclo[3.2.0]heptane-2-carboxylic acid
3-acetyl-6β-(α-carboxyphenylacetylamino)-7-oxo-1,3-diazabicyclo[3.2.0]heptane-2-carboxylic acid
3-acetyl-6β-(4-fluorophenylacetylamino)-7-oxo-1,3-diazabicyclo[3.2.0]heptane-2-carboxylic acid
3-acetyl-6β-(3-hydroxyphenylacetylamino)-7-oxo-1,3-diazabicyclo[3.2.0]heptane-2-carboxylic acid
3-acetyl-7-oxo-6β-(4-trifluoromethylphenylacetylamino)-7-oxo-1,3-diazabicyclo[3.2.0]heptane-2-carboxylic acid.

EXAMPLE 5

When an acid chloride listed below:

propionyl chloride
butyryl chloride
valeryl chloride is substituted in the procedure of Example 1 for acetyl chloride in the reaction with N-(cis-4-oxo-3-phenoxyacetyl-amino-2-azetidinylmethyl)iminoacetic acid benzyl ester, the following compounds of this invention are obtained:

7-oxo-6β-phenoxyacetylamino-3-propionyl-1,3-diazabicyclo[3.2.0]heptane-2-carboxylic acid benzyl ester IR: 5.57μ(β-lactam); 5.7μ(ester); ca. 6.00μ(amides)
3-butyryl-7-oxo-6β-phenoxyacetylamino-1,3-diazabicyclo[3.2.0]heptane-2-carboxylic acid benzyl ester
7-oxo-6β-phenoxyacetylamino-3-valeryl-1,3-diazabicyclo[3.2.0]heptane-2-carboxylic acid benzyl ester.

Removal of the benzyl ester protecting group as previously described or by other standard methods gives the carboxylic acid compounds of this invention listed below:

- 7-oxo-6β-phenoxyacetylamino-3-propionyl-1,3-diazabicyclo[3.2.0]heptane-2-carboxylic acid
- 3-butyryl-7-oxo-6β-phenoxyacetylamino-1,3-diazabicyclo[3.2.0]heptane-2-carboxylic acid
- 7-oxo-6β-phenoxyacetylamino-3-valeryl-1,3-diazabicyclo[3.2.0]heptane-2-carboxylic acid.

Similarly, 3-propionyl, butyryl and valeryl derivatives of the other 7-oxo-1,3-diazabicyclo[3.2.0]-heptane-2-carboxylic acid compounds disclosed herein are prepared.

EXAMPLE 6

Substitution of chloroformate listed below:

methyl chloroformate
ethyl chloroformate
propyl chloroformate
butyl chloroformate in the procedure of Example 1 in place of acetyl chloride in the reaction with N-(cis-4-oxo-3-phenoxyacetylamino-2-azetidinylmethyl)iminoacetic acid benzyl ester gives the following compounds of this invention:

- 3-methoxycarbonyl-7-oxo-6β-phenoxyacetylamino-1,3-diazabicyclo[3.2.0]heptane-2-carboxylic acid benzyl ester
- 3-ethoxycarbonyl-7-oxo-6β-phenoxyacetylamino-1,3-diazabicyclo[3.2.0]heptane-2-carboxylic acid benzyl ester IR:5.56μ (β-lactam); 5.66μ (ester); 5.85 and 5.90μ (amides and carbonate)
- 7-oxo-6β-phenoxyacetylamino-3-propoxycarbonyl-1,3-diazabicyclo[3.2.0]heptane-2-carboxylic acid benzyl ester
- 3-butoxycarbonyl-7-oxo-6β-phenoxyacetylamino-1,3-diazabicyclo[3.2.0]heptane-2-carboxylic acid benzyl ester.

Removal of the benzyl ester protecting group as previously described or by other standard methods gives the carboxylic acid compounds of this invention listed below:

- 3-methoxycarbonyl-7-oxo-6β-phenoxyacetylamino-1,3-diazabicyclo[3.2.0]heptane-2-carboxylic acid
- 3-ethoxycarbonyl-7-oxo-6β-phenoxyacetylamino-1,3-diazabicyclo[3.2.0]heptane-2-carboxylic acid
- 7-oxo-6β-phenoxyacetylamino-3-propoxycarbonyl-1,3-diazabicyclo[3.2.0]heptane-2-carboxylic acid
- 3-butoxycarbonyl-7-oxo-6β-phenoxyacetylamino-1,3-diazabicyclo[3.2.0]heptane-2-carboxylic acid.

In like manner, 3-alkoxycarbonyl derivatives of the other 7-oxo-1,3-diazabicyclo[3.2.0]heptane-2-carboxylid acid compounds described above are prepared.

EXAMPLE 7

When a halo- or dihaloacetyl halide listed below:

bromoacetyl bromide
chloroacetyl chloride
dichloroacetyl chloride
difuoroacetyl chloride is substituted in the procedure of Example 1 in place of acetyl chloride in the reaction with N-(cis-4-oxo-3-phenoxyacetylamino-2-azetidinylmethyl)iminoacetic acid benzyl ester, the following compounds are obtained:

- 3-bromoacetyl-7-oxo-6β-phenoxacetylamino-1,3-diazabicyclo[3.2.0]heptane-2-carboxylic acid benzyl ester
- 3-chloroacetyl-7-oxo-6β-phenoxyacetylamino-1,3-diazabicyclo[3.2.0]heptane-2-carboxylic acid benzyl ester
- 3-dichloroacetyl-7-oxo-6β-phenoxyacetylamino-1,3-diazabicyclo[3.2.0]heptane-2-carboxylic acid benzyl ester
- 3-difluoroacetyl-7-oxo-6β-phenoxyacetylamino-1,3-diazabicyclo[3.2.0]heptane-2-carboxylic acid benzyl ester.

Removal of the benzyl ester protecting group as previously described or by other standard methods gives the carboxylic acid compounds of this invention listed below:

- 3-bromoacetyl-7-oxo-6β-phenoxyacetylamino-1,3-diazabicyclo-[3.2.0]heptane-2-carboxylic acid
- 3-chloroacetyl-7-oxo-6β-phenoxyacetylamino-1,3-diazabicyclo[3.2.0]heptane-2-carboxylic acid
- 3-dichloroacetyl-7-oxo-6β-phenoxyacetylamino-1,3-diazabicyclo[3.2.0]heptane-2-carboxylic acid
- 3-difluoroacetyl-7-oxo-6β-phenoxyacetylamino-1,3-diazabicyclo[3.2.0]heptane-2-carboxylic acid

EXAMPLE 8

Substitution of a benzoyl chloride listed below:

benzoyl chloride
p-toluoyl chloride
o-toluoyl chloride
4-t-butylbenzoyl chloride
p-anisoyl chloride
2-bromobenzoyl chloride
3-chlorobenzoyl chloride
4-fluorobenzoyl chloride
3-trifluoromethylbenzoyl chloride in the procedure of Example 1 in place of acetyl chloride in the reaction with N-(cis-4-oxo-3-phenoxyacetylamino-2-azetidinylmethyl)iminoacetic acid benzyl ester gives the following compounds of this invention:

- 3-benzoyl-7-oxo-6β-phenoxyacetylamino-1,3-diazabicyclo[3.2.0]heptane-2-carboxylic acid benzyl ester
- 7-oxo-6β-phenoxyacetylamino-3-(p-toluoyl)-1,3-diazabicyclo[3.2.0]heptane-2-carboxylic acid benzyl ester IR: 5.58μ (β-lactam); 5.70μ (ester); 5.90, 5.96, 6.10μ (amides)
- 7-oxo-6β-phenoxyacetylamino-3-(o-toluoyl)-1,3-diazabicyclo[3.2.0]heptane-2-carboxylic acid benzyl ester
- 3-(4-t-butylbenzoyl)-7-oxo-6β-phenoxyacetylamino-1,3-diazabicyclo[3.2.0]heptane-2-carboxylic acid benzyl ester
- 3-(p-anisoyl)-7-oxo-6β-phenoxyacetylamino-1,3-diazabicyclo[3.2.0]heptane-2-carboxylic acid benzyl ester; mp 148°–150°
- 3-(2-bromobenzoyl)-7-oxo-6β-phenoxyacetylamino-1,3-diazabicyclo[3.2.0]heptane-2-carboxylic acid benzyl ester
- 3-(3-chlorobenzoyl)-7-oxo-6β-phenoxyacetylamino-1,3-diazabicyclo[3.2.0]heptane-2-carboxylic acid benzyl ester 3-(4-fluorobenzoyl)-7 oxo-6β-phenoxyacetyl-amino-1,3-diazabicyclo[3.2.0]heptane-2-carboxylic acid benzyl ester 7-oxo-6β-phenoxyacetylamino-3-(3-trifluoromethylbenzoyl)-1,3-diazabicyclo[3.2.0]heptane-2-carboxylic acid benzyl ester.

Removal of the benzyl ester protecting group as previously described or by other standard methods gives the carboxylic acid compounds of this invention listed below:

3-benzoyl-7-oxo-6β-phenoxyacetylamino-1,3-diazabicyclo[3.2.0]heptane-2-carboxylic acid 7-oxo-6β-phenoxyacetylamino-3-(p-toluoyl)-1,3-diazabicyclo[3.2.0]heptane-2-carboxylic acid 7-oxo-6β-phenoxyacetylamino-3-(o-toluoyl)-1,3-diazabicyclo[3.2.0]heptane-2-carboxylic acid 3-(4-t-butylbenzoyl)-7-oxo-6β-phenoxyacetylamino-1,3-diazabicyclo[3.2.0]heptane-2-carboxylic acid 3-(p-anisoyl)-7-oxo-6β-phenoxyacetylamino-1,3-diazabicyclo[3.2.0]heptane-2-carboxylic acid 3-(2-bromobenzoyl)-7-oxo-6β-phenoxyacetylamino-1,3-diazabicyclo[3.2.0]heptane-2-carboxylic acid 3-(3-chlorobenzoyl)-7-oxo-6β-phenoxyacetylamino-1,3-diazabicyclo[3.2.0]heptane-2-carboxylic acid 3-(4-fluorobenzoyl)-7-oxo-6β-phenoxyacetylamino-1,3-diazabicyclo[3.2.0]heptane-2-carboxylic acid 7-oxo-6β-phenoxyacetylamino-3-(3-trifluoromethylbenzoyl)-1,3-diazabicyclo[3.2.0]heptane-2-carboxylic acid.

Similarly, the other 7-oxo-1,3-diazabicyclo[3.2.0]-heptane-2-carboxylic acid esters disclosed herein may be acylated with a benzoyl chloride listed above to give the corresponding compounds of this invention.

EXAMPLE 9

When a phenylacetyl chloride listed below:

phenylacetyl chloride
o-tolylacetyl chloride
p-tolylacetyl chloride
3-methoxyphenylacetyl chloride
4-methoxyphenylacetyl chloride
4-chlorophenylacetyl chloride
4-bromophenylacetyl chloride
4-fluorophenylacetyl chloride
3-trifluoromethylphenylacetyl chloride is substituted in the procedure of Example 1 for acetyl chloride in the reaction with N-(cis-4-oxo-3-phenoxyacetylamino-2-azetidinylmethyl) iminoacetic acid benzyl ester, the following compounds of this invention are obtained:

7-oxo-6β-phenoxyacetylamino-3-phenylacetyl-1,3-diazabicyclo[3.2.0]heptane-2-carboxylic acid benzyl ester 7-oxo-6β-phenoxyacetylamino-3-(o-tolylacetyl)-1,3-diazabicyclo[3.2.0]heptane-2-carboxylic acid benzyl ester 7-oxo-6β-phenoxyacetylamino-3-(p-tolylacetyl)-1,3-diazabicyclo[3.2.0]heptane-2-carboxylic acid benzyl ester 3-(3-methoxyphenylacetyl)-7-oxo-6β-phenoxyacetylamino-1,3-diazabicyclo[3.2.0]heptane-2-carboxylic acid benzyl ester 3-(4-methoxyphenylacetyl)-7-oxo-6β-phenoxyacetylamino-1,3-diazabicyclo[3.2.0]heptane-2-carboxylic acid benzyl ester 3-(4-chlorophenylacetyl)-7-oxo-6β-phenoxyacetylamino-1,3-diazabicyclo[3.2.0]heptane-2-carboxylic acid benzyl ester 3-(4-bromophenylacetyl)-7-oxo-6β-phenoxyacetylamino-1,3-diazabicyclo[3.2.0]heptane-2-carboxylic acid benzyl ester 3-(4-fluorophenylacetyl)-7-oxo-6β-phenoxyacetylamino-1,3- diazabicyclo[3.2.0]heptane-2-carboxylic acid benzyl ester 7-oxo-6β-phenoxyacetylamino-3-(3-trifluoromethylphenylacetyl)-1,3-diazabicyclo[3.2.0]heptane-2-carboxylic acid benzyl ester.

Removal of the benzyl ester protecting group as previously described or by other standard methods gives the carboxylic acid compounds of this invention listed below:

7-oxo-6β-phenoxyacetylamino-3-phenylacetyl-1,3-diazabicyclo[3.2.0]heptane-2-carboxylic acid 7-oxo-6β-phenoxyacetylamino-3-(o-tolylacetyl)-1,3-diazabicyclo[3.2.0]heptane-2-carboxylic acid 7-oxo-6β-phenoxyacetylamino-3-(p-tolylacetyl)-1,3-diazabicyclo[3.2.0]heptane-2-carboxylic acid 3-(3-methoxyphenylacetyl)-7-oxo-6β-phenoxyacetylamino-1,3- diazabicyclo[3.2.0]heptane-2-carboxylic acid 3-(4-methoxyphenylacetyl)-7-oxo-6β-phenoxyacetylamino-1,3-diazabicyclo[3.2.0]heptane-2-carboxylic acid 3-(4-chlorophenylacetyl)-7-oxo-6β-phenoxyacetylamino-1,3-diazabicyclo[3.2.0]heptane-2-carboxylic acid 3-(4-bromophenylacetyl)-7-oxo-6β-phenoxyacetylamino-1,3-diazabicyclo[3.2.0]heptane-2-carboxylic acid 3-(4-fluorophenylacetyl)-7-oxo-6β-phenoxyacetylamino-1,3-diazabicyclo[3.2.0]heptane-2-carboxylic acid 7-oxo-6β-phenoxyacetylamino-3-(3-trifluoromethylphenylacetyl)-1,3-diazabicyclo[3.2.0]heptane-2-carboxylic acid.

Similarly, 3-phenylacetyl and substituted phenylacetyl derivatives of the other 7-oxo-1,3-diazabicyclo-[3.2.0]heptane-2-carboxylic acid compounds disclosed herein are prepared.

EXAMPLE 10

When a substituted sulfonyl chloride listed below:

methanesulfonyl chloride
ethanesulfonyl chloride
benzenesulfonyl chloride
α-toluenesulfonyl chloride
p-toluenesulfonyl chloride is reacted with N-(cis-4-oxo-3-phenoxyacetylamino-2-azetidinylmethyl)iminoacetic acid benzyl ester according to the procedure described in Example 1, the following compounds of this invention are prepared:

3-methanesulfonyl-7-oxo-6β-phenoxyacetyl-amino-1,3-diazabicyclo[3.2.0]heptane-2-carboxylic acid benzyl ester; mp 117°–120°

3-ethanesulfonyl-7-oxo-6β-phenoxyacetylamino-1,3-diazabicyclo[3.2.0]heptane-2-carboxylic acid benzyl ester 3-benzenesulfonyl-7-oxo-6β-phenoxyacetylamino-1,3-diazabicyclo[3.2.0]heptane-2-carboxylic acid benzyl ester 7-oxo-6β-phenoxyacetylamino-3-α-toluenesulfonyl-
1,3-diazabicyclo[3.2.0]heptane-2-carboxylic acid
benzyl ester 7-oxo-6β-phenoxyacetylamino-3-p-toluenesulfonyl-
1,3-diazabicyclo[3.2.0]heptane-2-carboxylic acid
benzyl ester.

Removal of the benzyl ester protecting group as previously described or by other standard methods gives the carboxylic acid compounds of this invention listed below:

3-methanesulfonyl-7-oxo-6β-phenoxyacetylamino-
1,3-diazabicyclo[3.2.0]heptane-2-carboxylic acid 3-ethanesulfonyl-7-oxo-6β-phenoxyacetylamino-1,3-
diazabicyclo[3.2.0]heptane-2-carboxylic acid 3-benzenesulfonyl-7-oxo-6β-phenoxyacetylamino-
1,3-diazabicyclo[3.2.0]heptane-2-carboxylic acid 7-oxo-6β-phenoxyacetylamino-3-(α-toluene-sulfonyl)-1,3-diazabicyclo[3.2.0]heptane-2-carboxylic acid 7-oxo-6β-phenoxyacetylamino-3-(p-toluenesulfonyl)-1,3-diazabicyclo[3.2.0]heptane-2-carboxylic acid.

Similarly, the 3-substituted sulfonyl derivatives of the other 7-oxo-1,3-diazabicyclo[3.2.0]heptane-2-carboxylic acids disclosed herein are prepared.

EXAMPLE 11

3-Formyl-7-oxo-6β-phenoxyacetylamino-1,3-
diazabicyclo[3.2.0]-heptane-2-carboxylic acid To a solution of ca. 18 mg (0.38 mmole) of formyl fluoride and 40 μl (0.50 mole) of pyridine in 2.0 ml of anhydrous methylene chloride at −33° under argon is added a solution of 100 mg (0.25 mmole) of N-(cis-4-oxo-3-phenoxyacetylamino-2-azetidinylmethyl-)iminoacetic acid benzyl ester in 1.0 ml of anhydrous methylene chloride. The reaction mixture is allowed to slowly warm to ambient temperature overnight and then is poured into ethyl acetate and extracted with pH 7.0 buffer. The organic layer is dried ($MgSO_4$), filtered and the solvents are removed in vacuo to afford 3-formyl-7-oxo-6β-phenoxyacetylamino-1,3-diazabicyclo[3.2.0]heptane-2-carboxylic acid benzyl ester.

Alternatively, 3-formyl-7-oxo-6β-phenoxyacetylamino-1,3-diazabicyclo[3.2.0]heptane-2-carboxylic acid benzyl ester is prepared by substituting formyl imidazole and a catalytic amount of imidazole hydrochloride in place of formyl fluoride in the above procedure.

Removal of the benzyl ester protecting group as previously described or by other standard methods gives the title compound.

EXAMPLE 12

By use of 2,2,2-trichloroethylglyoxalate in the procedure of Example 1 in place of benzyl glyoxalate with subsequent treatment of the product with acetyl chloride as described therein, 3-acetyl-7-oxo-6β-phenoxyacetylamino-1,3-diazabicyclo[3.2.0]heptane-2-carboxylic acid 2,2,2-trichloroethyl ester is prepared.

In a similar manner, other esters of the 1,3-diazabicyclo[3.2.0]heptane-2-carboxylic acid compounds of this invention may be prepared.

What is claimed is:

1. A compound of the formula:

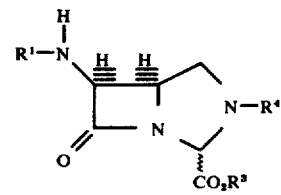

in which:

$R^1$ is hydrogen or

$R^2$ is phenyl; phenoxymethyl; benzyl; α-aminobenzyl; α-hydroxybenzyl; α-carboxybenzyl; phenyl substituted with lower alkyl of from one to four carbon atoms, lower alkoxy of from one to four carbon atoms, trifluoromethyl, halo or hydroxy; or benzyl substituted on the phenyl ring with lower alkyl of from one to four carbon atoms, lower alkoxy of from one to four carbon atoms, trifluoromethyl, halo or hydroxy;

$R^3$ is hydrogen or an easily removable ester protecting group; and $R^4$ is alkanoyl of from one to five carbon atoms; alkoxycarbonyl of from two to five carbon atoms; haloacetyl; dihaloacetyl; benzoyl; benzoyl substituted with lower alkyl of from one to four carbon atoms, lower alkoxy of from one to four carbon atoms, trifluoromethyl or halo; phenylacetyl; phenylacetyl substituted on the phenyl ring with lower alkyl of from one to four carbon atoms, lower alkoxy of from one to four carbon atoms, trifluoromethyl or halo; methanesulfonyl; ethanesulfonyl; benzenesulfonyl; α-toluenesulfonyl or p-toluenesulfonyl.

2. A compound as claimed in claim 1 in which $R^3$ is an easily removable ester protecting group.

3. A compound as claimed in claim 1 in which $R^3$ is hydrogen.

4. A compound as claimed in claim 2 in which $R^3$ is 2,2,2-trichloroethyl, $C_4$-$C_6$-tertiary alkyl, $C_5$-$C_7$-tertiary alkenyl, $C_5$-$C_7$-tertiary alkynyl, $C_1$-$C_6$-alkanoylmethyl, N-phthalimidomethyl, benzoylmethyl, naphthoylmethyl, furoylmethyl, thienoylmethyl, nitrobenzoylmethyl, halobenzoylmethyl, methylbenzoylmethyl, methanesulfonylbenzoylmethyl, phenylbenzoylmethyl, benzyl, nitrobenzyl, methoxybenzyl, benzyloxymethyl, nitrophenyl, methoxyphenyl, benzhydroyl, trityl, trimethylsilyl or triethylsilyl.

5. A compound as claimed in claim 4 in which $R^3$ is 2,2,2-trichloroethyl, t-butyl, benzyl, benzhydryl, benzyloxymethyl, p-nitrophenyl, p-methoxyphenyl, p-nitrobenzyl or p-methoxybenzyl.

6. A compound as claimed in claim 5 in which $R^4$ is acetyl, propionyl, ethoxycarbonyl, p-anisoyl, p-toluoyl or methanesulfonyl.

7. A compound as claimed in claim 6 in which $R^1$ is hydrogen.

8. A compound as claimed in claim 6 in which $R^1$ is

9. A compound as claimed in claim 8 in which $R^2$ is phenoxymethyl.

10. A compound as claimed in claim 9 being the compound 3-acetyl-7-oxo-6β-phenoxyacetylamino-1,3-diazabicyclo[3.2.0]heptane-2-carboxylic acid benzyl ester.

11. A compound as claimed in claim 3 in which $R^4$ is acetyl, propionyl, ethoxycarbonyl, p-anisoyl, p-toluoyl or methanesulfonyl.

12. A compound as claimed in claim 11 in which $R^1$ is hydrogen.

13. A compound as claimed in claim 11 in which $R^1$ is

14. A compound as claimed in claim 12 being the compound 3-acetyl-6β-amino-7-oxo-1,3-diazabicyclo[3.2.0]-heptane-2-carboxylic acid.

15. A compound as claimed in claim 13 in which $R^2$ is phenoxymethyl.

16. A compound as claimed in claim 15 being the compound 3-acetyl-7-oxo-6β-phenoxyacetylamino-1,3-diazabicyclo[3.2.0]heptane-2-carboxylic acid.

* * * * *